United States Patent [19]

Magerlein

[11] 3,989,735
[45] Nov. 2, 1976

[54] 4,5-CIS-DIDEHYDRO-PGB$_1$ ANALOGS
[75] Inventor: Barney J. Magerlein, Portage, Mich.
[73] Assignee: The Upjohn Company, Kalamazoo, Mich.
[22] Filed: Nov. 7, 1975
[21] Appl. No.: 629,884

Related U.S. Application Data
[60] Division of Ser. No. 440,629, Feb. 7, 1974, Pat. No. 3,933,889, which is a continuation-in-part of Ser. No. 247,993, April 27, 1972, abandoned.

[52] U.S. Cl. .................. 260/468 D; 260/488 R; 260/514 D
[51] Int. Cl.$^2$ .................................. C07C 177/00
[58] Field of Search ......... 260/468 D, 514 D, 488 R

[56] References Cited
OTHER PUBLICATIONS
Von Dorp, Annals of N.Y. Acad. Sci., 180, 181, 1971.

*Primary Examiner*—Robert Gerstl
*Attorney, Agent, or Firm*—Morris L. Nielsen

[57] ABSTRACT

This invention is a group of 4,5-didehydro PG$_1$ (prostaglandin-type) analogs having variable chain length, branching and fluoro substitution in the hydroxy-substituted side-chain, and processes for making them. These compounds are useful for a variety of pharmacological purposes, including anti-ulcer, inhibition of platelet aggregation, increase of nasal patency, labor inducement at term, and wound healing.

32 Claims, No Drawings

4,5-CIS-DIDEHYDRO-PGB₁ ANALOGS

CROSS REFERENCE TO RELATED APPLICATIONS

This is a division of application Ser. No. 440,629, filed Feb. 7, 1974, now U.S. Pat. No. 3,933,889, which is a continuation-in-part of copending application Ser. No. 247,993, filed Apr. 27, 1972, now abandoned.

BACKGROUND OF THE INVENTION

This invention relates to novel compositions of matter, to novel methods for producing those, and to novel chemical intermediates useful in those processes. Particularly, this invention relates to certain novel analogs of known prostaglandins in which a cis carbon-carbon double bond links C-4 and C-5 in the carboxy-terminated chain.

The essential material for this application, including the background of the invention, the disclosure of the invention, and the description of the preferred embodiments, including Preparations and Examples, is incorporated by reference from U.S. Pat. No. 3,933,889 columns 1–50, inclusive, under the provisions of M.P.E.P. 608.01(p).

SUMMARY OF THE INVENTION

It is a purpose of this invention to provide novel 4,5-didehydro $PG_1$ analogs in which a cis carbon-carbon double bond links C-4 and C-5 in the carboxy-terminated chain and in which there is variable chain length, branching, and fluoro substitution in the hydroxy-substituted side chain. It is a further purpose to provide 4,5-didehydro-13,14-dihydro-$PG_1$ analogs. It is a further purpose to provide esters, lower alkanoates, and pharmacologically acceptable salts of said analogs. It is a further purpose to provide novel processes for preparing these acids and esters. It is still a further purpose to provide novel intermediates useful in said processes.

The presently described acids and esters of the 4,5-unsaturated prostaglandin analogs include compounds of the following formulas, and also the racemic compounds of each respective formula and the mirror image thereof:

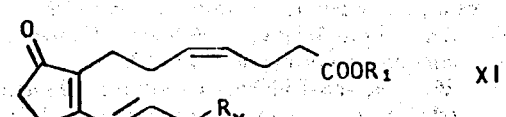

XI

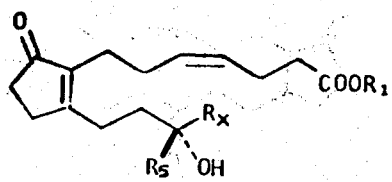

XV

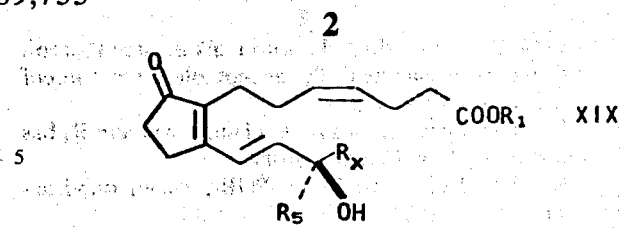

XIX

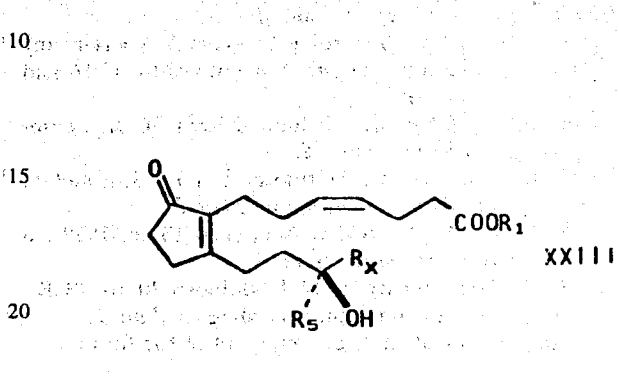

XXIII

In Formulas XI, XV, XIX, and XXIII, $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one to 3 chloro or alkyl of one to 4 carbon atoms, inclusive; $R_5$ is hydrogen, methyl, or ethyl; $R_x$ is (1) alkyl of 2 to 4 carbon atoms, inclusive, substituted with zero to 2 fluoro, inclusive, (2) branched-chain alkyl of 5 carbon atoms or alkyl of 5 carbon atoms substituted with one or 2 fluoro, or (3) alkyl of 6 to 10 carbon atoms, inclusive, substituted with zero to 2 fluoro, inclusive; and the wavy line ∼ indicates attachment to the cyclopentane ring in alpha or beta configuration.

I claim:

1. An optically active compound of the formula

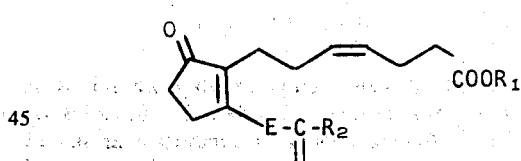

or a racemic compound of that formula and the mirror image thereof, wherein M is

or

wherein $R_5$ is hydrogen, methyl, or ethyl; wherein $R_1$ is hydrogen or alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; wherein $R_2$ is alkyl of 2 to 4 carbon atoms, inclusive, substituted with zero to 2 fluoro, inclusive; and wherein E is trans-CH=CH— or —$CH_2CH_2$—; including the lower alkanoates thereof, and the pharmacologically acceptable salts thereof when $R_1$ is hydrogen.

2. A compound according to claim 1 wherein $R_2$ has a chain length of 4 carbon atoms.

3. 4,5-cis-Didehydro-20-nor-$PGB_1$, a compound according to claim 2.

4. 4,5-cis-Didehydro-20-nor-$PGB_1$, methyl ester, a compound according to claim 2.

5. A compound according to claim 2 wherein any fluoro substitution is at either or both of the C-16 and C-17 carbon atoms.

6. 4,5-cis-Didehydro-16-fluoro-20-nor-$PGB_1$, a compound according to claim 5.

7. 4,5-cis-Didehydro-16-fluoro-20-nor-$PGB_1$, methyl ester, a compound according to claim 5.

8. 4,5-cis-Didehydro-16,16-difluoro-20-nor-$PGB_1$, a compound according to claim 5.

9. 4,5-cis-Didehydro-16,16-difluoro-20-nor-$PGB_1$, methyl ester, a compound according to claim 5.

10. An optically active compound of the formula

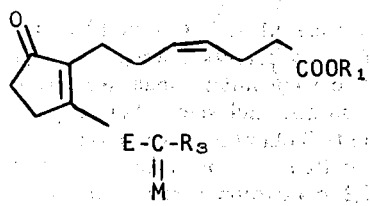

or a racemic compound of that formula and the mirror image thereof, wherein M is

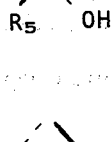

or

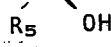

wherein $R_5$ is hydrogen, methyl, or ethyl; wherein $R_1$ is hydrogen or alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; wherein $R_3$ is branched-chain alkyl of 5 carbon atoms or alkyl of 5 carbon atoms substituted with one or 2 fluoro; and wherein E is trans-CH=CH— or —$CH_2CH_2$—; including the lower alkanoates thereof, and the pharmacologically acceptable salts thereof when $R_1$ is hydrogen.

11. A compound according to claim 10 wherein $R_3$ is alkyl of 5 carbon atoms substituted with one or 2 fluoro.

12. A compound according to claim 11 wherein any branching or fluoro substitution is at either or both of the C-16 and C-17 carbon atoms.

13. 4,5-cis-Didehydro-16-fluoro-$PGB_1$, a compound according to claim 12.

14. 4,5-cis-Didehydro-16-fluoro-$PGB_1$, methyl ester, a compound according to claim 12.

15. 4,5-cis-Didehydro-16,16-difluoro-$PGB_1$, a compound according to claim 12.

16. 4,5-cis-Didehydro-16,16-difluoro-$PGB_1$, methyl ester, a compound according to claim 12.

17. An optically active compound of the formula

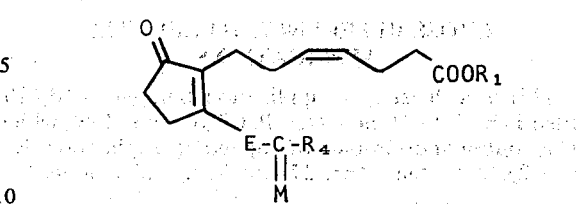

or a racemic compound of that formula and the mirror image thereof, wherein M is

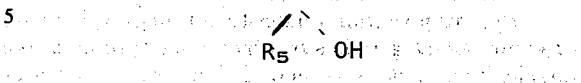

or

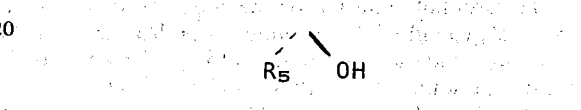

wherein $R_5$ is hydrogen, methyl, or ethyl; wherein $R_1$ is hydrogen or alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; and wherein $R_4$ is alkyl of 6 to 10 carbon atoms, inclusive, substituted with zero to 2 fluoro, inclusive; and wherein E is trans-CH=CH— or —$CH_2CH_2$—; including the lower alkanoates thereof, and the pharmacologically acceptable salts thereof when $R_1$ is hydrogen.

18. A compound according to claim 17 wherein $R_4$ has a chain length of 6 carbon atoms.

19. A compound according to claim 18 wherein any branching of fluoro substitution is at either or both of the C-16 and C-17 carbon atoms.

20. 4,5-cis-Didehydro-20-methyl-$PGB_1$, a compound according to claim 19.

21. 4,5-cis-Didehydro-20-methyl-$PGB_1$, methyl ester, a compound according to claim 19.

22. 4,5-cis-Didehydro-16-methyl-$PGB_1$, a compound according to claim 19.

23. 4,5-cis-Didehydro-16,16-dimethyl-$PGB_1$, a compound according to claim 19.

24. 4,5-cis-Didehydro-16,16-dimethyl-$PGB_1$, methyl ester, a compound according to claim 19.

25. 4,5-cis-Didehydro-16-fluoro-20-methyl-$PGB_1$, a compound according to claim 19.

26. 4,5-cis-Didehydro-16-fluoro-20-methyl-$PGB_1$, methyl ester, a compound according to claim 19.

27. 4,5-cis-Didehydro-16,16-difluoro-20-methyl-$PGB_1$, a compound according to claim 19.

28. 4,5-cis-Didehydro-16,16-difluoro-20-methyl-$PGB_1$, methyl ester, a compound according to claim 19.

29. An optically active compound of the formula

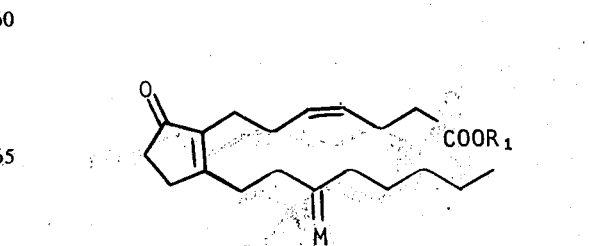

or a racemic compound of that formula and the mirror image thereof, wherein M is

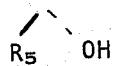

or

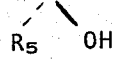

wherein $R_5$ is hydrogen, methyl, or ethyl; and wherein $R_1$ is hydrogen or alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; including the lower alkanoates thereof, and the pharmacologically acceptable salts thereof when $R_1$ is hydrogen.

30. A compound according to claim 29 wherein M is

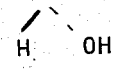

31. 4,5-cis-Didehydro-13,14-dihydro-$PGB_1$, a compound according to claim 30.

32. 4,5-cis-Didehydro-13,14-dihydro-$PGB_1$, methyl ester, a compound according to claim 30.

* * * * *